United States Patent
Atkinson et al.

(10) Patent No.: US 7,946,150 B2
(45) Date of Patent: May 24, 2011

(54) DETECTION SYSTEMS

(75) Inventors: Jonathan Richard Atkinson, Watford (GB); Stephen John Taylor, Hyde Heath (GB); Paul Grant Wynn, Broxted (GB)

(73) Assignee: Smiths Detection-Watford Limited, London (GB)

( * ) Notice: Subject to any disclaimer, the term of this patent is extended or adjusted under 35 U.S.C. 154(b) by 406 days.

(21) Appl. No.: 11/989,013

(22) PCT Filed: Jul. 20, 2006

(86) PCT No.: PCT/GB2006/002701
§ 371 (c)(1),
(2), (4) Date: Jan. 18, 2008

(87) PCT Pub. No.: WO2007/010261
PCT Pub. Date: Jan. 25, 2007

(65) Prior Publication Data
US 2009/0174412 A1    Jul. 9, 2009

(30) Foreign Application Priority Data

Jul. 20, 2005  (GB) .................................. 0514840.8
Dec. 3, 2005   (GB) .................................. 0524769.7

(51) Int. Cl.
*G01N 7/00* (2006.01)
(52) U.S. Cl. .................................................... 73/19.01
(58) Field of Classification Search ................. 73/19.01, 73/23.2
See application file for complete search history.

(56) References Cited

U.S. PATENT DOCUMENTS

| | | | |
|---|---|---|---|
| 4,388,342 A * | 6/1983 | Suzuki et al. | 427/8 |
| 4,551,624 A | 11/1985 | Spangler et al. | |
| 5,554,846 A * | 9/1996 | Regiec et al. | 250/288 |
| 5,587,581 A * | 12/1996 | Stroosnyder | 250/287 |
| 5,814,281 A * | 9/1998 | Williams et al. | 422/88 |
| 6,459,079 B1 | 10/2002 | Machlinski et al. | |
| 6,495,824 B1 | 12/2002 | Atkinson | |
| 6,534,765 B1 * | 3/2003 | Robb et al. | 250/288 |
| 6,825,460 B2 | 11/2004 | Breach et al. | |
| 6,854,317 B2 * | 2/2005 | Porter et al. | 73/31.05 |
| 7,168,294 B2 * | 1/2007 | Porter et al. | 73/31.05 |
| 7,456,390 B2 * | 11/2008 | Miller et al. | 250/287 |
| 7,488,971 B2 * | 2/2009 | Kobayakawa et al. | 257/13 |

FOREIGN PATENT DOCUMENTS

| | | |
|---|---|---|
| EP | 0 596 978 B1 | 3/1997 |
| GB | 2 316 490 A | 2/1998 |
| GB | 2 323 165 A | 9/1998 |
| GB | 2 324 407 A | 10/1998 |
| GB | 2 324 875 A | 11/1998 |
| WO | WO 93/01485 | 1/1993 |
| WO | WO 97/28444 | 8/1997 |
| WO | WO 2004/102611 A2 | 11/2004 |
| WO | WO 2005/060696 A2 | 7/2005 |

* cited by examiner

*Primary Examiner* — Hezron Williams
*Assistant Examiner* — Rodney T Frank
(74) *Attorney, Agent, or Firm* — Foley & Lardner LLP

(57) ABSTRACT

An IMS system or the like has dopant contained in a way such that it is only released when needed. The dopant could be contained in a device (50) similar to an ink-jet printer and released as droplets (55) when required. Alternatively, the dopant could be trapped in material (156) of a molecular sieve (150) in such a way that it is not normally released into air flowing through the sieve but can be released by energising a heater (157) in the sieve.

18 Claims, 2 Drawing Sheets

DETECTION SYSTEMS

This invention relates to detection systems of the kind by which a vapour or gas can be analysed, the system including a contained quantity of dopant substance.

Ion mobility spectrometers or IMS systems are often used to detect substances such as explosives, drugs, blister and nerve agents or the like. An IMS system typically includes a detector cell to which a sample of air containing a suspected substance is supplied as a gas or vapour. The cell operates at or near atmospheric pressure and contains electrodes energized to produce a voltage gradient along the cell. Molecules in the sample of air are ionized, such as by means of a radioactive source, UV source or by corona discharge, and are admitted into the drift region of the cell by an electrostatic gate at one end. The ionized molecules drift to the opposite end of the cell at a speed dependent on the size of the ion. By measuring the time of flight along the cell it is possible to identify the ion. It is common practice to add a reagent or dopant to the cell. The reagent is added to modify the ion-molecule reaction chemistry to achieve at least two aims. One aim is to prevent the ionisation of molecules of low electron or low proton affinity such that they are not detected and hence reduce the opportunity for false alarms. Another aim is to alter the position of one or more ion peaks in the mobility spectrum such that they are shifted from a position close to or neighbouring a peak produced by the compounds to be detected. In this manner the compounds to be detected are more easily identified and quantified. Mass spectrometers may also make use of dopants or reagents.

Examples of IMS systems are described in GB 2324407, GB 2324875, GB2316490, GB2323165, U.S. Pat. No. 4,551, 624, U.S. Pat. No. 6,459,079, WO2004/102611 and U.S. Pat. No. 6,495,824. There are various ways in which a dopant can be added to the drift chamber. Usually the dopant is administered via a permeation source. Alternatively, U.S. Pat. No. 6,825,460 describes an IMS system having a molecular sieve for drying and cleaning recirculated gases, which is impregnated with a dopant. One problem with previous doping arrangements is that it can be difficult to control the level of dopant material that is administered. It can also be difficult to switch between different dopants.

It is an object of the present invention to provide an alternative detection system.

According to one aspect of the present invention there is provided a detection system of the above-specified kind, characterised in that the system is arranged to release small quantities of the dopant substance for detection purposes at selected times only.

The system may be arranged to discharge the dopant in droplets. The system may include a piezoelectric device arranged to discharge dopant from a reservoir. Alternatively, the system may include a heater arranged to discharge dopant from a reservoir. The dopant may be contained in a sieve in such a way that the dopant is not normally released, the sieve including an arrangement for acting on the dopant to release the dopant from the sieve when desired. The arrangement for acting on the dopant may include a device for heating the sieve material, and the heating device may be an electrical resistance heater. The detection system preferably includes an IMS or mass spectrometer.

According to another aspect of the present invention there is provided a method of detecting the presence of a substance including the step of supplying a sample gas or vapour to detection apparatus, characterised in that the method includes the step of selectively releasing small quantities of dopant substance to dope the sample gas or vapour.

Small quantities of dopant may be released by applying heat or pressure to dopant in a container.

According to a further aspect of the present invention there is provided a detection system by which a vapour or gas can be analysed, characterised in that the system includes a reservoir of a dopant liquid and an arrangement for discharging the dopant liquid from the reservoir in droplet form.

According to a fourth aspect of the present invention there is provided a detection system by which a vapour or gas can be analysed, characterised in that the system includes a housing through which gas flows in the system, characterised in that the housing includes a dopant substance in a captured form where substantially none is released to the gas flow unless the system is activated selectively to release the dopant into the gas flow.

The system may be activated by applying heat or pressure to release the dopant into the gas flow. The system preferably includes an arrangement for removing dopant from the system.

According to a fifth aspect of the present invention there is provided an IMS detection system having a molecular sieve connected in a recirculating gas flow path, the sieve containing a dopant absorbed in the sieve material, characterised in that the system includes an arrangement for selectively modifying the sieve material to release dopant into the gas flow so that dopant is only released when the sieve material is selectively modified.

According to a sixth aspect of the present invention there is provided a method of detecting the presence of a substance including the step of supplying a sample gas or vapour to detection apparatus without a dopant, and selectively releasing dopant absorbed in a solid substance by modifying the substance.

IMS systems according to the present invention, will now be described, by way of example, with reference to the accompanying drawings, in which.

Figure 1:
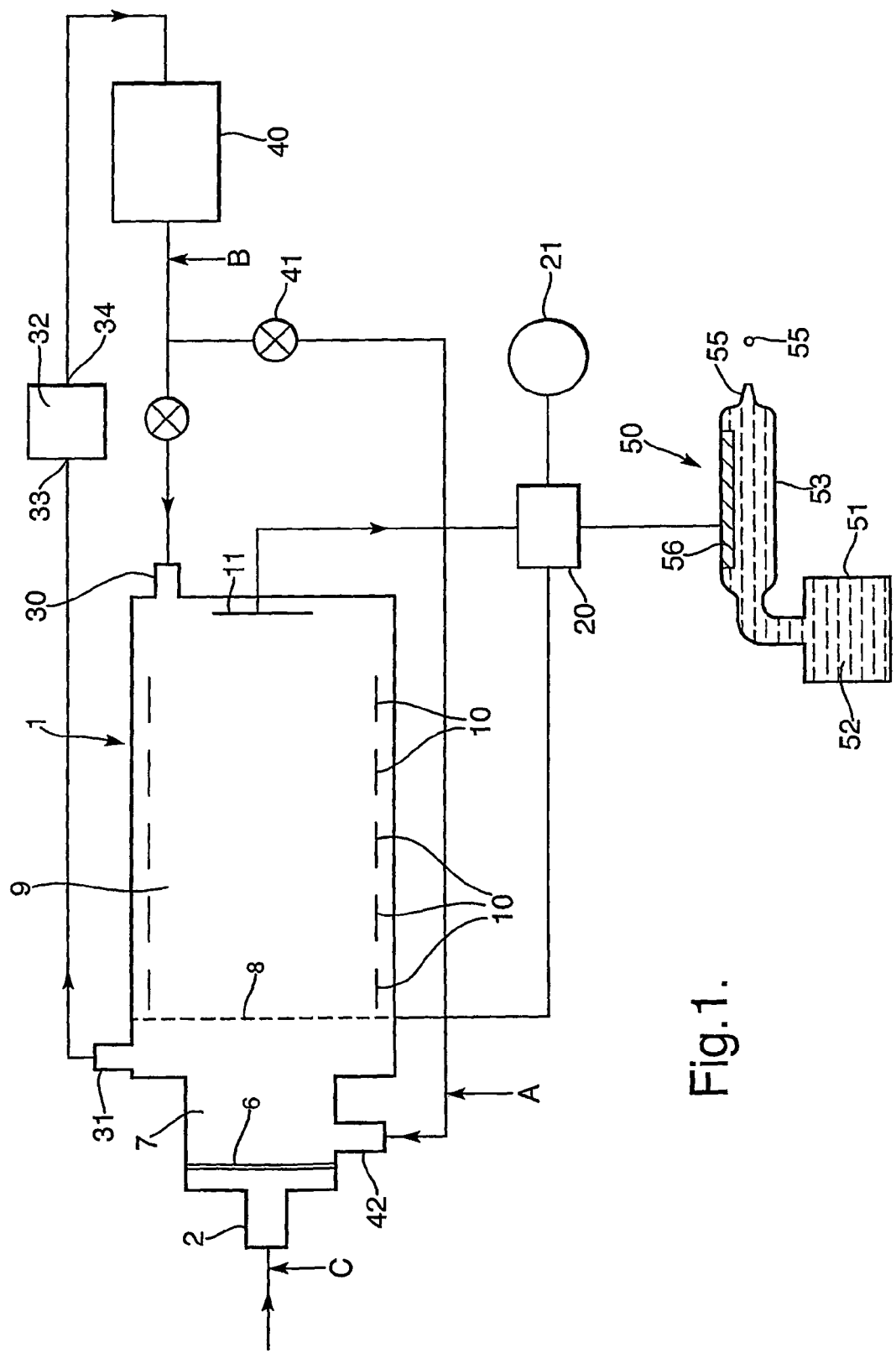
FIG. 1 shows one form of the system schematically.

With reference first to FIG. 1, the system includes an IMS drift cell 1 having an inlet port 2 by which sample air to be analysed is supplied to the apparatus. Typically, the flow rate of the inlet gas is about 800 ml/min. The port 2 opens into the left-hand end of the interior of the cell 1 via a selective barrier 6 such as a semi-permeable membrane, or of any other form that allows passage of the molecules of interest whilst excluding the majority of other molecules. Alternatively, the barrier 6 could be non-selective, such as a pinhole, as described in WO93/01485. Instead of a barrier, the sample to be analysed may be supplied to the cell 1 by some other interface, such as of the kind described in EP596978.

The barrier 6 communicates with an ionisation region 7 including an ionisation source such as a radiation source, UV source or a corona discharge. To the right of the ionisation region 7 a Bradbury Nielson gating grid 8 controls passage of ionised molecules into a drift region 9 formed by a series of drift electrodes 10. A collector plate 11 at the right-hand end of the cell 1 collects ions passed through the drift region 9 and provides an output to a processor 20, which also controls the gate 8 and various other functions of the system. The processor 20 provides an output to a display 21 or other utilisation means indicative of the nature of the sample.

At its right-hand end, the cell 1 has an inlet 30, by which recirculated, cleaned, dried drift gas is supplied to the interior of the cell where it travels from right to left and flows out via an exhaust outlet 31 close to the gating grid 8 in the ionisation region 7. The flow of drift gas is typically around 500 ml/min. Air is supplied to the inlet 30 by means of a pump 32 having an inlet 33 connected to the exhaust outlet 31 and an outlet 34 connected to a molecular sieve 40, which cleans and dries the air exhausted from the drift chamber 9. The outlet of the sieve 40 also connects via a valve 41 to an inlet 42 just downstream of the membrane 6 so that a source of clean air is circulated and mixes with the analyte vapours diffusing through the membrane. The flow rate of the source gas supplied to the inlet 42 is typically around 300 ml/min. The system downstream, to the right, of the membrane 6 forms a closed pneumatic system separated from atmosphere by the membrane.

As so far described, the system is conventional.

The system differs from previous IMS systems in the arrangement by which a dopant is administered to the analyte. In particular, the arrangement of FIG. 1 is such as to administer the dopant in the form of droplets. The preferred arrangement by which this is achieved includes an inkjet printer head device 50 or a similar device. The device 50 has a contained quantity of dopant such as in a reservoir or tank 51 containing the dopant substance 52 in a liquid form. Where the desired dopant is not normally in a liquid form it can be provided in a liquid form by dissolving in a suitable carrier liquid. The tank 51 opens into a propulsion chamber 53 having an outlet nozzle 54 by which droplets 55 of the liquid 52 are ejected. The propulsion chamber 53 can be of different forms. In one form, the chamber 53 includes a piezoelectric element 56, which is energised externally to apply a compressive force to the liquid in the chamber sufficient periodically to eject a droplet 55 from the nozzle 54. When the element 56 is de-energised a vacuum is created within the chamber 53, which draws in an extra bolus of liquid 52 from the tank 51. Typically, the volume of each droplet 55 is between about 8 and 10 picoliters. Alternatively, the propulsion chamber could include a thermal device, such as a resistor, which can be heated to expand the liquid in the chamber and force a droplet out of the nozzle.

The droplet administering device 50 can be connected to the system at various different locations. It could be located at point A to inject dopant to the source gas flow supplied to the inlet 42. It could be connected at point B to inject dopant into both the source gas flow to the inlet 42 and into the drift gas flow to the inlet 30. Alternatively, the droplet administering device 50 could be connected at point C to inject dopant into the inlet gas supplied to the port 2. Several devices containing the same dopant could be connected at different points in the system, such as at points A and C. Alternatively, several devices could be connected at the same point so that different amounts of dopant could be administered by discharging from one or both devices. In a system having several dopant administering devices, they could contain different dopants.

The arrangement of the present invention allows for very accurate control of dopant levels because of the very small amount of the dopant material released periodically in each droplet. Dopant levels can be controlled by altering the frequency at which droplets are administered or by altering the size of the droplets, which is possible with some forms of inkjet printer heads. Dopant levels can be varied rapidly and different dopants can be switched in and out of the system very quickly, as desired.

Although the dopant in the arrangement described above is administered as droplets, these rapidly vaporize so that the dopant becomes a vapour. Depending on the nature of the dopant, the apparatus may need to have provision for increasing vaporization, such as a heater or atomising device (not shown).

There are other ways than droplets in which small quantities of dopant can be released periodically. For example, microvalves could be used to release small quantities of a contained quantity of dopant periodically.

Figure 2:
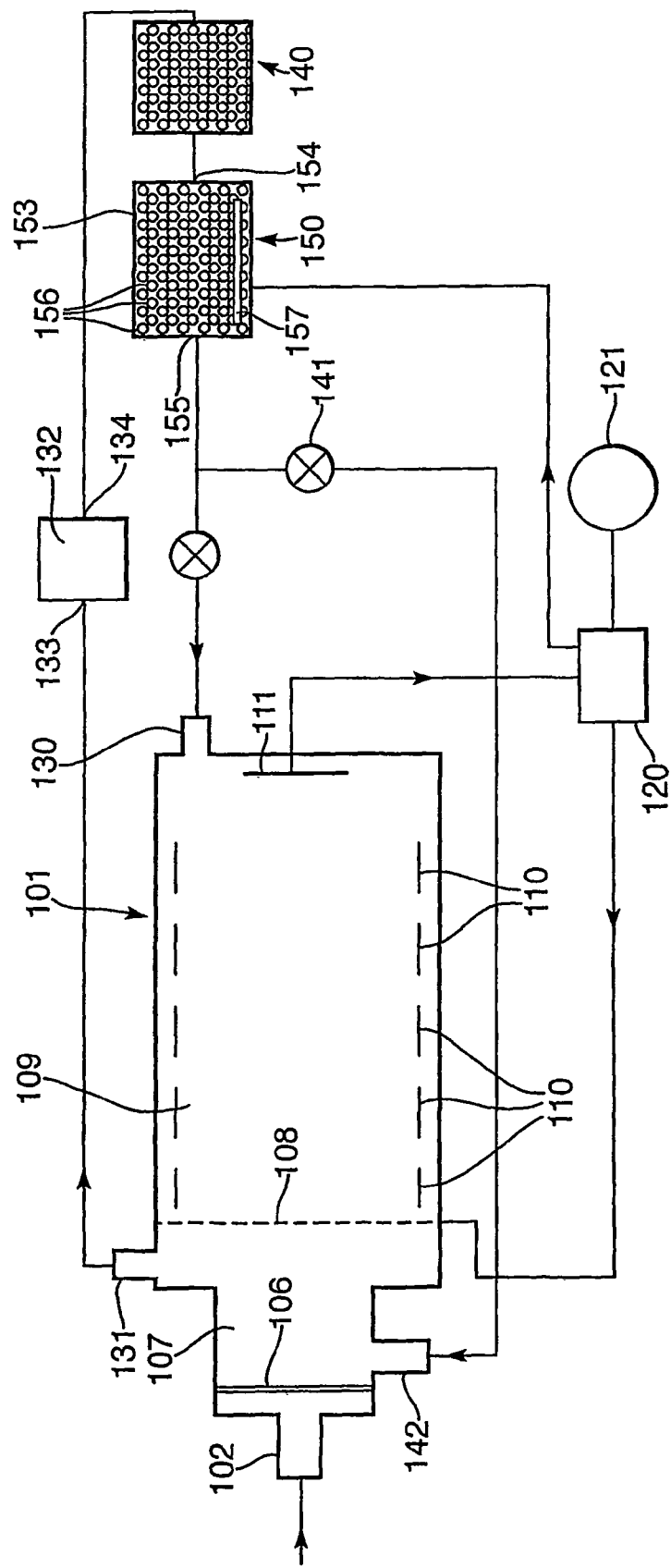
FIG. 2 shows another form of the system schematically

FIG. 2 shows an arrangement where a doped molecular sieve is used, with the dopant being contained and released by the application of heat. Features of the system shown in FIG. 2 that are equivalent to those in the system of FIG. 1 are given the same reference numerals with the addition of 100.

In place of the single molecular sieve in the arrangement of FIG. 1, the system of FIG. 2 has a two molecular sieves 140 and 150 connected to one another in series. The upstream molecular sieve 140 is conventional and acts to clean and dry gas supplied to it before supply to the downstream sieve 150. The downstream molecular sieve 150 includes an outer housing 153 of cylindrical form with an inlet 154 at one end and an outlet 155 at the opposite end. The housing 153 is packed with a large number of spheres 156, about 2 mm in diameter, of a solid material, such as zeolite. Gas flowing through the housing 153 follows a tortuous path around the outside of the spheres 156 with some of the gas flowing through the spheres. The solid material 156 contains a dopant substance absorbed within it. The solid material 156 and dopant are selected such that the dopant remains captured within the material, without release to the gas flow, until caused to do so by some selectively-operable means. In the present example, the selectively-operable means is an electrical resistance heater 157 mounted within the housing 153 and arranged to apply heat to the sieve material 156 when signalled to do so by the control unit 120. When the temperature of the sieve material 156 rises, a small amount of the dopant is released to the gas flow through the sieve 150. When the heater 157 is unenergised again, the temperature of the sieve material 156 rapidly drops, partly as a result of the gas flow through it, and no further dopant is released. Dopant circulating in the system is removed by the upstream sieve 140 so that the system reverts to the original undoped state. This arrangement enables dopant to be released rapidly when required and only when required. The system could be arranged to operate initially in an undoped state and, when it detects a substance, or when there is ambiguity about the identification of a substance, the control unit 120 energizes the heater 157 to release the dopant and enable a better identification of the substance.

The doped sieve material need not be heated by an electrical resistance heater, instead, an inductive, RF, microwave or optical/infrared radiation arrangement could be used to heat and release the dopant into the gas flow. There are various arrangements, other than thermal arrangements, that might be suitable to release a dopant substance from a captured state in a doped sieve. For example, reducing the gas pressure might enable the release of dopant. Alternatively, with some absorbent materials, applying an increased, squeeze pressure to the material might allow release of dopant. This could be accomplished by piezoelectric means. Alternatively, dopant could be released by adding another substance, such as water, to the dopant absorbant. Other techniques that might be suitable include vibration, such as at ultrasonic frequencies, or displacement of the absorbent material, such as to apply a centrifugal force.

Several sieves containing dopants could be employed in a system, such as connected together in series or parallel. In this way, by selectively activating different numbers of sieves, the amount of dopant released could be varied. Alternatively, the different sieves could contain different dopants so that the system can be doped differently as desired.

The arrangement of the present invention allows for the selective release of dopant as and when required. This gives a detection system flexibility in detecting different substances and also minimizes the consumption of dopant material, which can be a particular advantage in portable apparatus or where the dopant is hazardous or expensive.

Doped liposomes could be used where the dopant is contained within a liposome shell and released from the shell by the application of heat and/or pressure. Inert waxes could be used instead to make an impermeable seal between the dopant and the IMS airstream, with the wax seal being broken by the application of heat.

The invention is not confined to IMS systems but could be used in other doped detection systems, such as mass spectrometer systems.

The invention claimed is:

1. A detection system comprising:
   an ionization source configured to ionize a sample comprising a vapor or a gas to form ions; and
   a container configured to release, at a selected time, a quantity of a dopant sufficient to dope one or more of the sample or the ions to alter at least some of the ions' ion mobility, wherein the container comprises a propulsion chamber for releasing the dopant.

2. A detection system according to claim 1, wherein the system is arranged to release the dopant in droplets.

3. A detection system according to claim 1, wherein the system comprises a piezoelectric device arranged to release the dopant from the propulsion chamber.

4. A detection system according to claim 1, further comprising a sieve configured to retain the dopant, wherein the sieve comprises an arrangement for releasing the dopant from the sieve at the selected time.

5. A detection system according to claim 1, wherein the system comprises an ion mobility spectrometer (IMS) or mass spectrometer.

6. A detection system according to claim 1, further comprising an arrangement for removing the dopant from the system.

7. The detection system of claim 1, wherein the container is configured to selectively release dopant periodically.

8. A method of detecting a substance comprising:
   supplying a sample gas or vapor to detection apparatus;
   ionizing the gas or vapor to form ions; and
   selectively releasing a quantity of dopant to dope one or more of the sample or the ions, wherein the dopant alters at least some of the ions' ion mobility, and wherein the dopant is released from a propulsion chamber.

9. A method according to claim 8, wherein the quantities of dopant are released by applying heat or pressure to the dopant in a container.

10. The method of claim 8, wherein selectively releasing a quantity of dopant comprises modifying a substance, having dopant adsorbed thereto, to release the dopant.

11. A detection system comprising:
    an ionization source configured to ionize a sample comprising a vapor or a gas to form ions;
    a reservoir configured to contain a liquid dopant; and
    an arrangement comprising a propulsion chamber for discharging the dopant from the reservoir in droplet form, wherein the dopant alters at least some of the ions' ion mobility.

12. An IMS detection system comprising:
    an ionization source configured to ionize a sample comprising a vapor or a gas to form ions;
    a molecular sieve connected in a recirculating gas flow path, wherein the sieve can adsorb a dopant to retain the dopant, wherein the system comprises an arrangement for selectively modifying the sieve material to release dopant into the recirculating gas flow so that dopant is released when the sieve material is selectively modified, and wherein the dopant alters at least some of the ions' ion mobility; and
    a propulsion chamber for releasing dopant.

13. A detection system comprising:
    a container configured to retain a quantity of a dopant substance, wherein the container comprises a propulsion chamber; and
    a heater arranged to discharge dopant from the propulsion chamber, wherein the system is arranged to release, at a selected time, the dopant substance from the container to dope a vapor or gas sample for detection purposes.

14. A detection system comprising:
    a sieve, including sieve material, with a contained quantity of a dopant substance;
    a device for heating the sieve material; and
    a propulsion chamber for releasing dopant,
    wherein the dopant is contained in the sieve in such a way that the dopant is not normally released, and wherein activation of the device for heating the sieve material causes release of the dopant from the sieve.

15. A detection system according to claim 14, wherein the device is an electrical resistance heater.

16. A device for containing and releasing dopant comprising:
    a container configured to retain a quantity of dopant in liquid form;
    a propulsion chamber with an outlet nozzle, wherein the propulsion chamber is connected to the container to receive dopant from the container; and
    an arrangement for releasing, at a selected time, at least some of the dopant in the propulsion chamber.

17. The device according to claim 16, wherein the arrangement comprises a piezoelectric element that is configured to provide a compressive force to dopant in the propulsion chamber sufficient to release the dopant from the propulsion chamber.

18. The device according to claim 16, wherein the arrangement comprises a heating element that is configured to be heated to release the dopant from the propulsion chamber.

* * * * *